United States Patent [19]

Ghyczy et al.

[11] 4,273,679
[45] Jun. 16, 1981

[54] ALUMINUM ALLOYS HAVING A HIGH REDUCING CAPACITY AND PREPARATION THEREOF

[75] Inventors: Jenö Ghyczy,

[73] Assignee: Chinoin Gyogyszer es Vegyeszeti Termekek Gyara Rt., Budapest, Hungary

[21] Appl. No.: 44,034

[22] Filed: May 31, 1979

[30] Foreign Application Priority Data

Jun. 3, 1978 [HU] Hungary .................................. GI 278

[51] Int. Cl.³ .......................... B01J 21/04; B01J 23/44; B01J 23/72; B01J 23/74
[52] U.S. Cl. .................................. 252/466 J; 252/463; 252/466 PT; 252/466 B; 148/6.27; 427/327; 427/435
[58] Field of Search ................. 252/463, 466 J, 477 Q, 252/466 B, 466 PT; 427/327, 435; 148/6.27; 428/469

[56] References Cited

U.S. PATENT DOCUMENTS

| 2,290,364 | 7/1942 | Tosterud | 427/435 |
|---|---|---|---|
| 2,883,311 | 4/1959 | Halpert | 148/6.27 X |
| 3,544,485 | 12/1970 | Taira et al. | 252/477 Q |
| 3,619,300 | 11/1971 | Heller et al. | 148/6.27 X |
| 3,673,116 | 6/1972 | Richter | 252/477 Q |
| 3,781,227 | 12/1973 | Sokolsky et al. | 252/477 Q |
| 4,018,628 | 4/1977 | Paulet | 148/6.27 |
| 4,066,816 | 1/1978 | Sheasby et al. | 428/469 |

Primary Examiner—W. J. Shine
Attorney, Agent, or Firm—Karl F. Ross

[57] ABSTRACT

This invention relates to a process for the preparation of aluminum alloys having a high reducing capacity for use in reductions in organic chemistry. According to this method a discontinuous heterodisperse superficial alloy is formed by subjecting an aluminum alloy prepared by a metallurgical process to superficial activation and/or treating aluminum with a salt of a metal having a greater normal electrode potential than that of aluminum; whereby the solution of said metal in a protic solvent is reacted with granular aluminum and/or an aluminum alloy. The catalyst prepared according to the invention is especially suitable for the reduction of a nitro or nitroso group into an amino group. The aluminum alloys having a high reducing capacity are also within the scope of the invention.

20 Claims, No Drawings

ALUMINUM ALLOYS HAVING A HIGH REDUCING CAPACITY AND PREPARATION THEREOF

This invention relates to aluminum alloys having high reducing capacity and the application thereof in organic chemistry.

It is well known that aluminum, zinc and iron powder possess reducing properties. The reduction of compounds having nitro, nitroso or oxo groups has been described in a large number of publications, books and patents. In the pharmaceutical industry, and in the production of plant protecting agents and dyes, the reductions are carried out generally with zinc or iron powder or by means of catalytic hydrogenation (generally using a palladium or Raney-nickel catalyst). The use of aluminum is rarely reported and never on an industrial scale. According to experiments carried out on an industrial scale, when zinc powder is used the yield of the reduction step strongly varies depending on the quality of the metal; the situation is the same in the case of Bechamp reductions. For the above reason these metals are not frequently used, although they are cheaper than Raney-nickel, let alone the noble metal catalysts.

In laboratory-scale reductions aluminum-amalgam is most generally used. In industry it can, however, be applied only restrictedly since mercury contaminations are most strictly forbidden in the products. Furthermore the preparation of completely mercury-free products is very uneconomical due to the complicated purification techniques involved.

Additionally it is known that certain activating additives can be used. Crystalline iodine is the most popular activating additive of aluminum. The activating effect—i.e. the improvement of the reducing capacity of the metal—is however neither general nor reliable. While it works on certain substrates, the activated aluminum is quite ineffective if other chemical compounds are subjected to reduction. The activated aluminum improves the reduction of nitrobenzene but fails to work if sulfur-containing compounds—i.e. N-nitroso-imidazolidine-2-thion—are reduced. We have chosen this compound as the "model substrate" in our experiments, because by the conventional methods said compound cannot be subjected to catalytic hydrogenation, due to the catalyst poisoning properties thereof.

The aim and object of our invention is, therefore, the preparation of aluminum alloys having high reducing capacity from aluminum. The alloys can be generally used in organic chemistry also for the reduction of compounds which hitherto could be reduced only with difficulty.

According to another aspect of the present invention there is provided a process for the preparation of aluminum alloys having high reducing capacity and being useful in organic chemistry which comprises forming a heterodisperse superficial alloy by subjecting an aluminum alloy prepared by a metallurgical process to superficial (surface) activation and/or treating aluminum having whatever composition with a salt of a metal having a greater normal electrode potential than aluminum; whereby a solution of said metal salt in a protic solvent is reacted with granular aluminum or an aluminum alloy.

Aluminum alloys prepared by a metallurgical process may contain various metals in different amounts. The most frequently used alloying components are magnesium, zinc, silicon, copper, manganese, nickel, titanium and iron.

It has been found that in the preparation of aluminum alloys having a high reducing capacity, those metallurgically produced aluminum alloys can be used which comprise metals having a greater normal electrode potential than aluminum. From the metals those proved to be particularly preferable which are capable of the formation of ions having various degrees of oxidation and of forming a redox system. Iron is particularly advantageous. The amount of the metal having a higher normal electrode potential than aluminum has a strong influence on the reducing capacity of the alloy obtained after activation. It has been found that if iron is present it is preferred to use an aluminum alloy prepared by a metallurgical process comprising more iron than that present in the eutectic, particularly more than 2% iron.

The term "metallurgical process" encompasses all known and generally used procedures in the metallurgy of aluminum.

It has surprisingly been found that aluminum having a high reducing capacity in organic chemistry may be prepared by subjecting an aluminum alloy prepared by metallurgical processes to superficial activation. If necessary the oily contaminants may be removed from the surface of the aluminum alloy prior to activation.

In the first stage of activation the oxide layer is removed from the surface of the aluminum alloy obtained by a metallurgical process in order to obtain a pure metallic surface. The oxide layer may be removed by means of the acids and bases used in the course of activation, preferably with a mineral acid. It has been found that when activating an aluminum alloy prepared by a metallurgical process which contains metals having a normal electrode potential greater than that of aluminum, as a result of the action of the activating acid or base the metal salts are dissolved from the aluminum alloy into the protic medium, whereafter they precipitate on the surface of the aluminum alloy and form a heterodisperse superficial alloy. Due to a replacement reaction between the metal ions and the active aluminum surface, the precipitated metal forms discretely separated plaques on the surface of aluminum.

The said heterodisperse superficial (surface) alloy forms a characteristic discontinuous system which is responsible for the efficiency of the organic reduction reactions. According to our experiments the greater the heterodispersity of the metallurgically produced aluminum used as a starting material, the easier it is to form the discontinuous superficial alloy by means of the solutions of the metal ions in protic solvents. On the contrary, if the aluminum is pure it is more difficult to obtain a discontinuous heterodisperse superficial alloy. If the metallurgically produced aluminum alloy contains a sufficient amount of metals having a greater normal electrode potential than that of aluminum, the activating procedure produces a heterodisperse superficial alloy highly suitable for organic chemical reductions.

It has been found that the composition of the aluminum used as starting material is irrelevant. Aluminum alloys having high reducing capacity and applicable in organic chemistry for reducing purposes can be prepared from aluminum having whatever composition by treating the said aluminum and/or aluminium alloy with a solution of a salt of a metal having a greater normal electrode potential than that of aluminum in a protic solvent. As a protic solvent, an acid or base, preferably a mineral acid can be used in solutions formed with water or water-miscible organic solvents.

According to a preferred embodiment of our invention the heterodisperse superficial alloy may be readily formed by stirring aluminum and/or aluminum alloy in a solution of said metal salt in an alkaline, neutral or acidic medium at a temperature between 0° C. and 100° C. for 1-150 minutes. when aluminum of greater particle size is used (e.g. aluminum chips) the active surface becomes smaller. The suitable particle size of the aluminum is required to provide sufficiently great active surface in the reduction. The greater the active surface area of the discontinuous heterodisperse superficial surface, the quicker and more effective will be the reduction. For the preparation of the heterodisperse superficial alloy, an alkaline medium may be used if the superficial alloy is formed with the aid of amphoteric metal.

According to our discovery the heterodisperse superficial alloy may be obtained where the Al is alloyed with metals less noble than hydrogen, if the treatment is carried out with an acidic solution of the metal salt under heating, preferably at a temperature between 50° C. and 100° C. A heterodisperse iron containing superficial alloy having a high reducing capacity and readily applicable in organic chemistry may be prepared by treating aluminum and/or an aluminium alloy produced by a metallurgical process with a solution of an iron salt formed in 0.5 to 5 N hydrochloric acid at a temperature of 50° C. to 100° C. for 1 to 150 minutes.

It has been found that for the preparation of heterodisperse superficial aluminum alloys having high reducing capacity, preferably aluminium granules and/or aluminum alloy granules can be used as starting material. The particle size may vary within a wide range. The lower limit of the particle size is influenced by the fact that aluminum is highly susceptible to oxidation and if the particle size is too low the granule would consist exclusively of aluminum oxide and consequently there would be no metallic aluminum surface, which is essential for the formation of the heterodisperse superficial alloy. The upper limit of the particle size is defined by technological factors and the conditions of the reduction (e.g. by the rate of stirring).

The term "acid" used throughout the specification preferably relates to mineral acids such as hydrochloric acid, hydrobromic acid, nitric acid, sulfuric acid or phosphoric acid. The term "base" preferably covers alkali hydroxides (e.g. sodium or potassium hydroxide). The term "protic solvent" encompasses all suitable protic solvents preferably water, or lower alkanols (e.g. methanol or ethanol).

The salts of the metals having a greater normal electrode potential than that of aluminum may be salts having inorganic anions (e.g. chlorides, bromides, sulfates, nitrates, phosphates) or organic anions (e.g. formiates, acetates).

The particle size of the starting aluminum may vary within a wide range and preferably is 0.1 to 1.5 mm. The alloying metal content of the heterodisperse alloy may also vary within a wide range, such as 0.1 to 50%. In the case of iron it preferably is about 5% related to the weight of the aluminium.

According to a further feature of the present invention there are provided aluminum catalysts having a high reducing capacity and applicable in organic reductions prepared according to the process described above.

The catalysts of the present invention can be used in any reduction wherein a nitro or nitroso group is reduced into an amino group.

A preferred example of the application of the catalyst according to the present invention is the conversion of 1-nitroso-imidazolidin-2-thion into 1-amino-imidazolidin-2-thion, a valuable pharmaceutical intermediate which can be converted into potent antibacterial agents. According to prior art this reduction was carried by using zinc and an acid. It has been found that said reduction may be readily carried out with the aluminum alloy of the present invention. The advantage of the instant process is that metallic aluminum is much cheaper than zinc; moreover waste aluminum may also be used—so that the process according to the invention is more economical. A further advantage of our process is that aluminum is a more reactive and potent reducing agent than zinc. A further advantage resides in the fact that the technology is more readily feasible since the reaction mixture can be better stirred due to the smaller specific weight of aluminum.

According to the present invention there are provided aluminum alloys having high reducing capacity comprising a discontinuous heterodisperse superficial alloy comprising a metal having a greater normal electrode potential than that of aluminum. The said metal is preferably iron, tin, copper, zinc, lead, silver or palladium and, particularly, iron.

Further details of our invention are illustrated by the following Examples without any intention of limiting the scope of protection to the Examples.

EXAMPLE 1

27 g. of aluminium grains (aluminum content 97%; particle size: 0.5 to 1.5 mm.) are stirred in 1000 ml. of water with 15.0 g. sodium fluoride and the mixture is acidified with 13.0 ml. of concentrated sulfuric acid under cooling. The temperature is kept between 20° C. and 30° C. The mixture is stirred for 15 minutes whereupon 5 g. of crystalline cupric sulfate are added and the mixture is stirred until complete discoloration (about 15 to 20 minutes). The aqueous layer is decanted. The above procedure is carried out directly before the reduction is effected.

EXAMPLE 2

27 g. of aluminum grains are stirred in 200 ml. of N hydrochloric acid for 5 minutes, whereupon the metal is removed by filtration and allowed to stand in 200 ml. of a 0.1 N silver nitrate solution for half an hour. After decanting the aqueous solution the catalyst can be used for reduction.

EXAMPLE 3

27 g. of aluminum grains are activated with 200 ml. of N hydrochloric acid and 0.2 g. of palladium chloride at room temperature for an hour. Thereafter the catalyst is ready for use in reduction.

EXAMPLE 4

27 g. of aluminum grains are allowed to stand with 100 ml. of N hydrochloric acid and a solution of 5 g. of crystalline ferrous sulfate at 60° C. to 80° C. for an hour. After decanting the metal is washed with water. In the decanted liquid phase the concentration of iron ions amounts to 20 to 25 gamma/ml.

EXAMPLE 5

27 g. of aluminum grains (aluminum content 99.0%) are treated with iron according to the method described in Example 4. After washing the metal the above iron-treatment is repeated.

The aluminium grains obtained according to Examples 1 to 4 contain 97% of aluminum and can be more easily activated from the point of view of reducing capacity as a result of the accompanying metal content (iron, titanium, silicon).

EXAMPLE 6

27 g. aluminum grains (Al content 97%) are allowed to stand in a solution of 6 g. of crystalline zinc chloride and 300 ml. of 2 N sodium hydroxide for half an hour. After decanting and washing the metal may be directly used for reduction.

EXAMPLE 7

27 g. of aluminum grains (Al content 99%) are heated in 200 ml. of 0.1 N hydrochloric acid with 3 g. of copper powder for half an hour at 50° C. to 70° C. After cooling the metal is filtered off and may be used for reduction.

EXAMPLE 8

27 g. of aluminum scrapings (thickness 0.05 mm.) are refluxed in 300 ml. of trichloroethylene for 10 minutes. After cooling it is dried. The metal obtained, free from oil, is subjected to activation as described above.

EXAMPLE 9

The metal described in Example 8 is released and is subjected to the following treatment: 27 g. of the metal aluminum is allowed to stand in 500 ml. of water containing 5% sodium carbonate and 1% of trisodium phosphate at 50° C. to 60° C. for half an hour. The aqueous phase is removed by decanting while warm and the metal is washed to neutral with warm water.

EXAMPLE 10

The aluminum scrapings treated according to Example 8 and 9 (Al content 99%) is activated as follows: 27 g. of aluminum are heated in 200 ml. of methanol containing 1% of concentrated hydrochloric acid with 5 g. of ferric chloride at 40° C. to 50° C. for an hour. The mixture is cooled, whereupon the alcoholic solution is removed by decanting and the metal is dried.

EXAMPLE 11

27 g. of aluminum grains (Al content 99%) are activated in 200 ml. of a 40% aqueous acetic acid solution at 60° C. to 80° C. with 5 g. of cupric sulfate.

EXAMPLE 12

The metal once used may be recovered as follows: 27 g. of aluminum grains are washed with two 1000-ml. portions of 5% sulfuric acid, and then stirred with 500 ml. of a 1% potassium permanganate solution for an hour at 50° C. After decanting off of the liquid, the metal is washed with water (about 300 to 400 ml.).

EXAMPLE 13

123.1 g. of nitrobenzene are dissolved in a mixture of 300 ml. of water and 300 ml. of methanol, whereupon 200 g. of an aluminum treated according to Example 1 are added. To the mixture 800 ml. of concentrated hydrochloric acid are added under reflux, with stirring and cooling within 90 minutes. After cooling the metal is filtered off, the methanol is distilled off in vacuo and about 200 g. of sodium chloride are added. After standing for some hours the aniline can be separated. After fractionation 85 g. of aniline are obtained. Yield: 91%.

EXAMPLE 14

21.7 g. of freshly prepared crystalline 1-phenyl-2,3-dimethyl-4-nitroso-pyrazolone-5 are suspended in 200 ml. of ice cold water. 20 g. of aluminum grains—activated according to Example 5—are added, at a temperature between 0° C. and −10° C. under stirring, whereupon 100 ml. of concentrated hydrochloric acid are added dropwise. After 30 minutes the reaction mixture becomes colorless and the reduced product goes into solution. The metal is filtered off. Thus 18.3 g. of 1-phenyl-2,3-dimethyl-4-amino-pyrazolone-5 are obtained. Yield: 18.3 g., 90%.

EXAMPLE 15

51 g. of 1-nitroso-imidazolidin-2-thion are suspended in 700 ml. of icecold water and the solution is acidified with 40 ml. of acetic acid. 40 g. of sodium nitrite are added. The mixture is stirred at 10° C. for half an hour whereupon it is allowed to stand at 0° C. for 2 hours. In the meantime 50 g. of aluminum grains (Al content 97%) are activated with 10 g. of crystalline ferrous sulfate in 200 ml. of N hydrochloric acid at 60° C. to 80° C. for half an hour. The solution is removed by decanting and the aqueous suspension of N-nitroso-imidazolidin-2-thion is poured onto the metal. The temperature is kept between −5° C. and −12° C., under continuous stirring and cooling. Thereafter 200 ml. of cold (0° C. to 5° C.) concentrated hydrochloric acid are added dropwise within 40–45 minutes. The residual metal is filtered off, the solution containing the 1-amino-imidazolidin-2-thion is stirred with 70 g. of 5-nitro-furfural at 45° C. for half an hour, whereupon it is cooled to room temperature. The precipitated yellow crystals are filtered off, washed with water until free from acid, then washed with methanol and dried at 50° C. Thus 90 g. of 1-(5-nitrofurfurylidene-amino)-imidazolidin-2-thion are obtained. Yield: 75%.

We claim:

1. A process for the preparation of a discontinuous heterodisperse superficial aluminum alloy having a high reducing capacity which comprises the step of:
   superficially activating a granular aluminum alloy having a particle size of 0.1 to 1.5 mm wherein the alloying metal has a normal electrode potential greater than that of aluminum by treatment with an acid or base in the presence of a protic solvent to remove an oxide layer present on the aluminum alloy surface and to form in situ a precipitate of the alloying metal dissolved in the protic solvent.

2. The process defined in claim 1, step (a), wherein the alloying metal having a normal electrode potential greater than that of aluminum is selected from the group consisting of iron, tin, copper, zinc, lead, silver and palladium.

3. The process defined in claim 1, step (a), wherein the aluminum alloy is activated by treatment with a mineral acid.

4. The process defined in claim 1, step (a), wherein the alloying metal having a normal electrode potential greater than that of aluminum is selected from the group consisting of tin, copper, zinc, lead, silver and palladium along with at least 2% iron.

5. The process defined in claim 1, wherein step (a) is carried out at a temperature of 0° to 100° C. for a period of 1 to 150 minutes.

6. The process defined in claim 1, step (a), wherein the alloying metal having a normal electrode potential greater than that of aluminum is an amphoteric metal soluble under basic conditions.

7. The process defined in claim 1, step (a), wherein the alloying metal having a normal electrode potential greater than that of aluminum is a metal less noble than hydrogen and wherein the superficial activation of the aluminum is further carried out in the presence of an acidic solution of the metal salt.

8. The process defined in claim 7, step (a), wherein the alloying metal is iron and where the superficial activation of the aluminum alloy is carried out in the presence of an iron salt in 0.5 to 5 N hydrochloric acid at a temperature of 50° to 100° C.

9. The process defined in claim 1, wherein prior to step (a), oily impurities from the surface of the aluminum alloy are removed.

10. An aluminum alloy having high reducing capacity produced by the process defined in claim 1.

11. A process for the preparation of a discontinuous heterodisperse superficial aluminum alloy having a high reducing capacity which comprises the step of:
    treating granular aluminum or a granular aluminum alloy wherein said aluminum or aluminum alloy has a particle size of 0.1 to 1.5 mm with a solution of a salt of a metal having a greater normal electrode potential than that of aluminum in the presence of a protic solvent to precipitate the metal salt on the surface of the aluminum or aluminum alloy.

12. The process defined in claim 11, step (a), wherein the metal having a greater normal electrode potential than that of aluminum is selected from the group consisting of iron, tin, copper, zinc, lead, silver and palladium.

13. The process defined in claim 11, step (a), carried out at a temperature of 0° to 100° C. for a period of 1 to 150 minutes.

14. The process defined in claim 11, step (a), wherein the metal having a normal electrode potential greater than that of aluminum is an amphoteric metal soluble under basic conditions.

15. The process defined in claim 11, wherein prior to step (a), oily impurities from the surface of the aluminum alloy are removed.

16. An aluminum alloy having high reducing capacity produced by the process defined in claim 11.

17. The heterodisperse superficial aluminum alloy having a high reducing capacity produced according to the process of claim 1.

18. The heterodisperse superficial aluminum alloy having a high reducing capacity produced according to the process of claim 2.

19. The heterodisperse superficial aluminum alloy having a high reducing capacity produced according to the process of claim 11.

20. The heterodisperse superficial aluminum alloy having a high reducing capacity produced according to the process of claim 12.

* * * * *